United States Patent [19]

Fisher

[11] Patent Number: 4,724,843

[45] Date of Patent: Feb. 16, 1988

[54] TONOMETER

[75] Inventor: John Fisher, Royston, England

[73] Assignee: Keeler Limited, Berkshire, England

[21] Appl. No.: 866,298

[22] Filed: May 23, 1986

[30] Foreign Application Priority Data

May 23, 1985 [GB] United Kingdom ............... 8513108

[51] Int. Cl.⁴ .............................................. A61B 3/18
[52] U.S. Cl. ..................................... 128/648; 128/652
[58] Field of Search ........................ 128/645, 648, 652

[56] References Cited

U.S. PATENT DOCUMENTS

| | | | |
|---|---|---|---|
| 3,181,351 | 1/1965 | Stauffer | 128/645 |
| 3,232,099 | 2/1966 | Motchenbacher | 128/648 |
| 3,538,754 | 4/1971 | Grolman et al. | 128/648 |
| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 3,882,718 | 1/1975 | Kriebel | 128/648 |

FOREIGN PATENT DOCUMENTS 0164730  4/1985  European Pat. Off. ............ 128/648

OTHER PUBLICATIONS

Grolman, "American Optical Non-Content Tonometry", Opt. Eng., vol. 15, No. 4, pp. 312-320, Jul./1976.
Grolman, "Non-Contact Application Tonometry", The Optical, vol. 166, No. 4305, pp. 4, 8-10,16, 11/73.

Primary Examiner—Edward M. Cover
Attorney, Agent, or Firm—Oblon, Fisher, Spivak, McClelland & Maier

[57] ABSTRACT

A tonometer which comprises a casing adapted to be hand-held, said casing including an optical system (10 to 26) for forming a viewable image of the cornea of the eye (28), optical detecting means (32, 34A, 34B) for determining when the tonometer, which is by hand slowly moved around, is axially aligned with the cornea, means (40 to 58) for firing a controlled puff of air on to the cornea when a condition of stabilized alignment is determined, and circuitry responsive to the outputs of the optical detecting means for determining when a change in image contrast occurs due to applanation of the cornea, said puff firing means and said circuitry being adapted to measure the pressure at the eye when applanation is detected. The tonometer may take the form of a portable system in which at least some of the components are contained in a hand-held unit (100). Alternatively the tonometer may be bench-mounted.

20 Claims, 7 Drawing Figures

TONOMETER

DESCRIPTION

Field of the Invention

This invention relates to a tonometer, more especially of the non-contact type.

BACKGROUND TO THE INVENTION

It is known that, with certain disorders of the eye, such as glaucoma, there is a change from normal in the intraocular pressure in the eye. Measurement of the intraocular pressure is thus employed as a means of diagnosis.

PRIOR ART

One form of tonometer is operable by projecting a puff of fluid on to the surface of the cornea and optically detecting the applanation of the corneal surface which takes place. The pressure of the fluid pulse is controlled to increase until applanation occurs, and the pressure is determined at which applanation occurs. Generally, the pressure in the fluid delivery system increases with time for the duration of the puff, and it is assumed that a related pressure increase takes place at the eye, so that the applied pressure at which applanation occurs can be determined by a time measurement. Detection of applanation is by measurement of the amount of collected light.

Of known tonometers, the non-contact type is preferred, because the requirement for anaesthesia of the patient's cornea is avoided, but non-contact tonometers present greater problems in relation to initial alignment and with respect to pressure measurement. In particular, when the puff tube is spaced from the eye, the assumed relationship between the actual pressure at the eye and the determined pressure derived from the time measurement is open to doubt. Also, with regard to alignment, it can take a substantial time to set up the instrument ready for firing. In one known non-contacting tonometer, an alignment detection system including an occular is provided, and firing is positively prevented until alignment has been achieved.

A non-contacting tonometer such as has been referred to above is described in U.S. Pat. No. 3,756,073.

It is a general object of this invention to provide an improved tonometer which minimises or avoids the disadvantages referred to above.

THE INVENTION

According to one aspect of the invention, there is provided a tonometer comprising:
an optical system for forming, in conjunction with the reflecting surface of the cornea of the eye, an image of a target;
means for projecting a controlled-pressure fluid pulse on to the eye to distort the corneal surface and thereby produce change in the target image;
means for detecting the change in the image which occurs when the eye is distorted; and
means for outputting a value indicative of the pressure of the applied fluid pulse at the time when the change in contrast occurs.

By way of explanation, it should be made clear that it is found to be a more reliable and accurate way to gauge the shape of the corneal surface to measure image contrast than to rely, as in the prior art, on the total amount of collected light.

In this context the image contrast may be defined as the difference in light level between adjoining regions of interest in the image divided by the sum of the light levels from the same two regions.

This is not varied by the total amount of light as long as both the background and signal are proportional to the total amount of light.

Other measurements of image contrast are possible, the essential requirement being that the measurement is related to the relative brightness of a relatively bright image and a relatively dark image. In practice a simple ratio of the two brightness levels may be a convenient measurement. By measuring image contrast, the system enables high accuracy to be be achieved with high alignment tolerance.

In practice, image contrast can be measured by use of a plurality of photodetectors in an image plane, together with signal comparators and logic circuitry.

According to another aspect of the invention, there is provided a tonometer comprising:
an optical system for forming, in conjunction with the reflecting surface of the cornea of the eye, an image of a target;
means for detecting the initial condition of the target image to determine when the optical system has a selected predetermined location relative to the eye;
means associated with the optical system for projecting a controlled-pressure fluid pulse on to the eye to distort the corneal surface and thereby produce change in the target image;
means responsive to the target condition detecting means for causing operation of the fluid pulse projecting means when said selected predetermined location is attained; and
means for determining the pressure of the applied fluid pulse at the time when a given target image change occurs.

According to yet another aspect of the invention there is provided, a tonometer comprising:
a portable casing having a handgrip;
an optical system in the casing for forming, in conjunction with the reflecting surface of the cornea of the eye, an image of a target;
means in the casing for projecting a controlled-pressure fluid pulse on to the eye to distort the corneal surface and thereby produce change in the target image;
a fluid pressure delivery system which delivers fluid to said fluid pulse projecting means;
a switch associated with the handgrip and circuit means associated with the switch for arming the fluid pressure delivery system;
means for detecting the target image;
means for automatically effecting delivery of a controlled fluid pulse from the armed delivery system to the fluid pulse projecting means when the detecting means detects a given target condition; and
means for detecting a given change in the target image resulting from distortion of the corneal surface; and
means for determining the pressure of the applied pulse at the time when said given change in the target image occurs.

The invention thus provides means for effecting initial positioning with respect to the eye, including means which detects when correct positioning has been effected, the latter means controlling the fluid delivery system so that the fluid puff is automatically projected when correct positioning has been achieved. Such an arrangement is especially convenient in a hand-held tonometer, armed by operation of a switch, but not actually fired until, as the operator very slowly adjusts the location of the tonometer within a region of approximate alignment and distance which may be achieved by means of a viewing device, the condition of exact alignment and distance is attained. Such a method of use is considerably faster than the setting up procedure necessary with known tonometers.

The means of detecting correct positioning preferably comprises means for detecting central alignment by measuring the output of each of a plurality of off-axis photodetectors, for measuring the level of an on-axis photodetector and comparing it with the outputs of the off-axis detectors, and for ensuring that the conditions thus established are maintained for a sufficient time. The said means thus checks the system in respect of alignment, distance and stability. Provided the operator is, as is appropriate, only moving the tonometer very slowly within the region of approximate alignment, and the patient's eye is sufficiently stable, the detecting means will recognise the very slow movement through the correct location as a stable condition, and the tonometer will automatically be fired.

According to a still further aspect of the invention, there is provided a tonometer comprising:

an optical system for forming, in conjunction with the reflecting surface of the cornea of the eye, an image of a target;

means for projecting a controlled-pressure fluid pulse on to the eye to distort the corneal surface and thereby produce change in the target image;

means for detecting a given target change which occurs when the eye is distorted;

a pressure delivery system which delivers the fluid to said fluid pulse projecting means;

a pressure transducer for monitoring the pressure within a pressure delivery system;

means for matching the monitored pressure to the pressure applied to the corneal surface, whereby the pressure transducer provides a signal output indicative of the pressure applied to the eye at the time when a given target image change occurs.

Thus, in accordance with this aspect of the invention, the fluid pressure effective at the eye is measured, albeit indirectly. In a preferred arrangement this is achieved by providing a branch in the pressure delivery system where conditions are controlled to match the time/pressure profile to which the eye is subjected, and locating the pressure transducer in said branch. If the time/pressure profile is not available it can be determined by experiment.

The invention will now be described by way of example with reference to the accompanying drawings.

DETAILED DESCRIPTION OF ILLUSTRATED EMBODIMENTS

Figure 1:
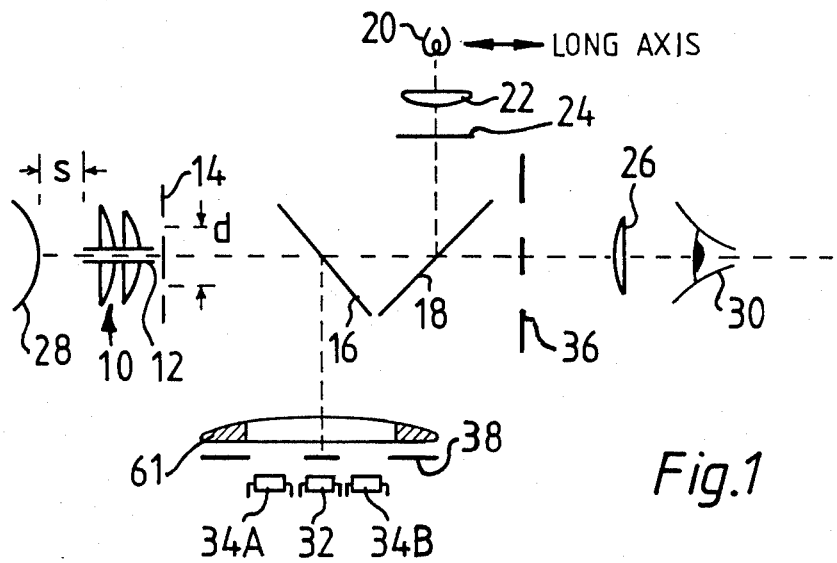
FIG. 1 shows a tonometer optical system.

Referring to FIG. 1, the basic optical system comprises an objective lens 10 and puff tube 12, a target 14, beam-splitters 16, 18, optical source arrangement comprising filament lamp 20, lens 22 and filter 24, and eyepiece lens 26. The cornea being tested is indicated at 28 and the eye of the operator at 30. Image detectors comprise on-axis detector 32 and off-axis detectors 34A, 34B. An aerial image is referenced 36. Another image 38 is formed at the photodetectors 32, 34A, 34B.

For alignment, the patient's eye is placed at a distance equal to the focal length (f) of the lens 10 of the fluid impulse tube (sometimes referred to as a puff tube). In this condition a major proportion of the light incident on the cornea is reflected back into the puff tube lens. However, other distances are also possible, particularly f/2.

The size of the filament in lamp 20 and the design of the optical system is such that the blurr size of the light spot on the cornea is approximately 3 mm in diameter. This ensures that the measured area during the applanation event is similar to that conventionally used.

The observer uses the eyepiece lens 26 to view the aerial image 36 and thus to obtain rough alignment and distance of the instrument relative to the patient's cornea 28.

A deep red filter 24 is used to limit the amount of light incident on the patient's cornea 28 to a safe level whilst ensuring that sufficient energy is available in the images for the observer to achieve alignment and for the detector to monitor the situation.

The components of the optical system and, in particular, the dimensions of the filament (or a controlled image of the filament), its distance from the first lens 22 and the focal length and diameter of this lens, the design, diameter and focal length of the objective lens 10, the design and position of the target 14 and the distance, size and position of the detector 32,34, are optimised to provide a well behaved variation in the contrast signal with curvature of the eye.

Details of a practical design are as follows filament lamp 20 with precision positioned filament filament dimension—3 mm×1 mm oriented with the long axis as shown in FIG. 1.

first lens 22, plano convex glass, focal length 14 mm, diameter 14 mm target object 14 etched in chromium on glass, two transparent squares, 4 mm×4 mm, whose pitch is approximately the same as the pitch of the photodetectors (or proportional thereto where optical magnification in the system allows.

position of target object, approximately 10 mm from the back face of the rear element of the objective lens 10 objective lens 10, two equal plano convex plastic elements to provide a composite focal length f of 20 mm. The diameter of the elements is 14 mm photodetectors 32, 34A, 34B, three photodiodes 2.7 mm×2.7 mm active area with a pitch of 3.5 mm.

The patient is positioned so that the cornea of the eye under investigation is at the focus of the objective lens. Under these circumstances the two images 36, 38 of the target object are formed at about 140 mm from the objective lens and they are approximately at 1 to 1 magnification. The image is formed by the objective lens combined with the convex reflecting face of the cornea. As the cornea becomes flattened by the applied air pulse the image moves towards the objective lens and the defocus combined with the deliberate aberration of the system causes a progressive degradation in image contrast in the plane of the photodetector.

Thus when the localised portion of the cornea which is used for imaging becomes distorted by an applied fluid pulse the contrast in the image reduces and the signals from the photodetectors are used to measure this reduction. The measurement can be related to the intraocular pressure as measured with conventional instruments at applanation, and thus it provides a measure of intraocular pressure This contrast reduction is referred to hereinafter as the applanation event.

Contrast may be defined as follows:

Contrast $(C) = (S_1 - S_2)/(S_1 + S_2)$ where:
$S_1$ = mean signal from the two outer photodetectors.
$S_2$ = signal from inner photodetector.

Figure 2:
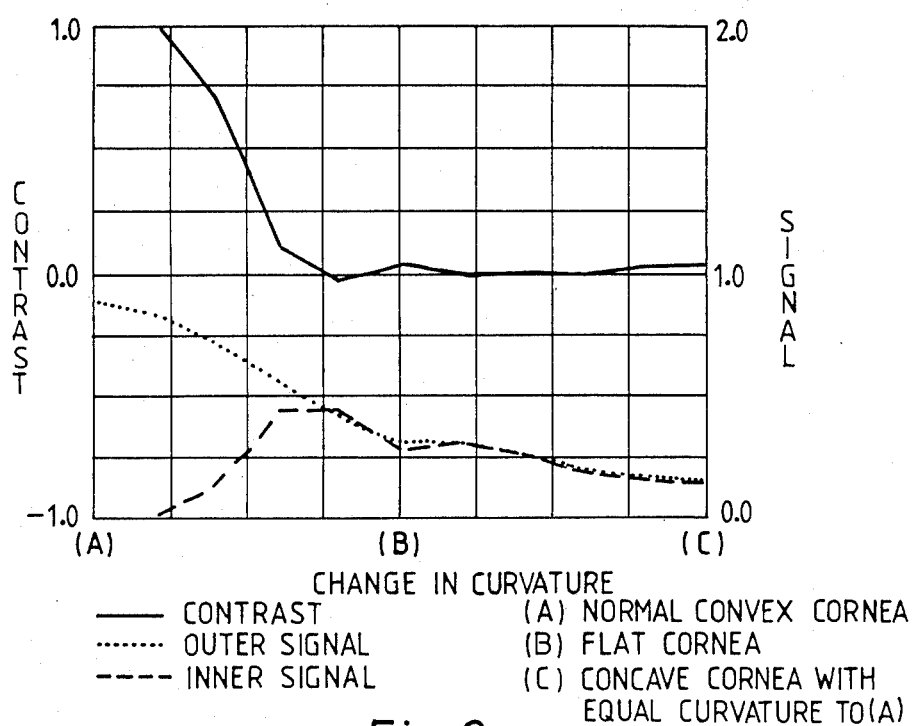
FIGS. 2 and 3 are explanatory diagrams related to detecting means employed in the tonometer.
Figure 3:
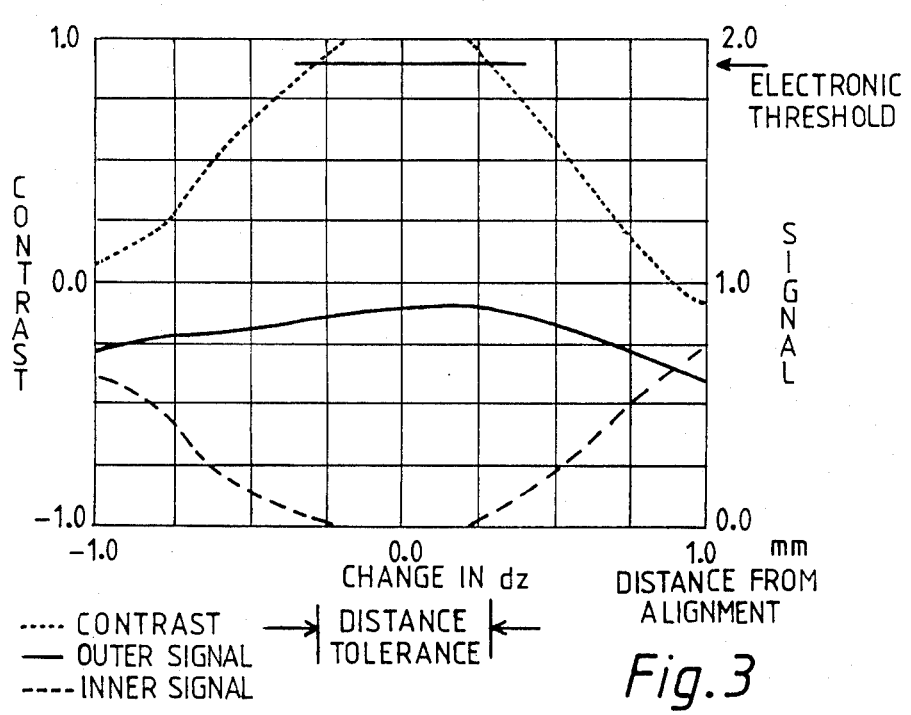

The theoretical variation for contrast vs corneal curvature is shown in FIG. 2, whilst FIG. 3 shows the distance sensitivity of the contrast and signal. This latter variation is used to determine that the instrument is the correct distance from the eye.

In practice, it is found satisfactory to gauge contrast by monitoring the ratio of $S_1$ to $S_2$ and this is the manner in which the electronic system subsequently to be described operates.

Figure 4:
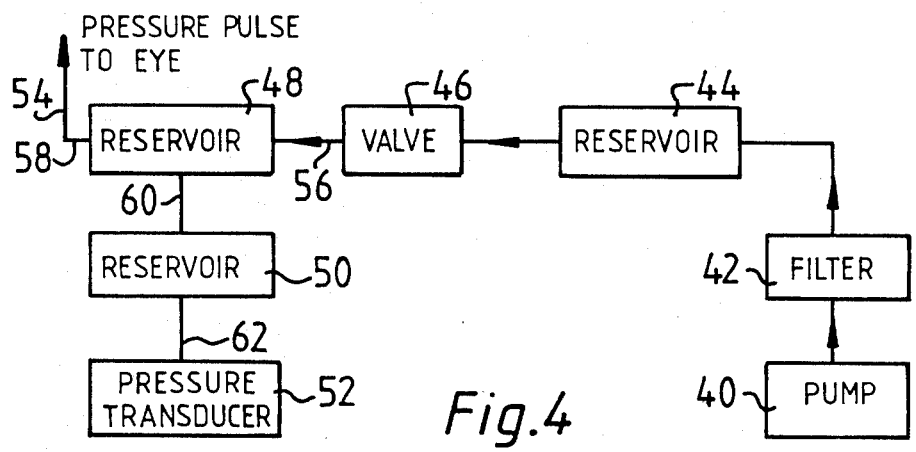
FIG. 4 shows a fluid pulse delivery system.

The pressure delivery system is shown in FIG. 4, and comprises pump 40, filter 42, first reservoir 44, solenoid-operable valve 46, second reservoir 48, and branch line comprising reservoir 50 and pressure transducer 52. The pressure pulse to the eye is delivered at 54. The shape of the pressure pulse applied to the eye is controlled by the impedances of pipes 56 and 58 and the volume and shape of reservoir 48.

In order to match the time/pressure profile of the pulse detected by the pressure transducer 52 to that received by the eye, the impedances of the pipes 60 and 62 and the volume and shape of reservoir 50 are controlled.

The electronic circuit (to be described) measuring the output of the pressure transducer 52 is calibrated to provide a reading on a display which corresponds to the pressure incident on the cornea at the alignment distance.

In an alternative embodiment pipe 60 is made equal in length, diameter and impedance to pipe 58 and reservoir 50 is replaced by an air space to pressure transducer 52. The gap between the end of tube 60 and the transducer 52 is set to be the same as that between the end of tube 58 and the patient's cornea, when the instrument is correctly aligned. The transducer 52 is in this case preferably spherically shaped, with the same radius of curvature as an average human cornea. A suitable transducer 52 can be produced, for example, using a silicon strain gauge device filled with oil or grease and connected to a metal sphere covered with a resilient material such as rubber.

Alignment is gauged from three criteria all being simultaneously achieved. Under these circumstances a reliable measurement can be taken and the combination of signals from the associated electronic monitoring systems is used to initiate the fluid impulse (sometimes simply referred to as a puff) and record the applanation event. The criteria are as follows:

1. That the image is correctly centred on the photodetectors. This is determined by measuring the light intensity on the two outer photodetectors 34A, 34B. If both detectors measure a signal greater than a predetermined level the associated electronic system produces a signal which indicates that the centration alignment is satisfactory. Thus the axis of the patient's cornea is then correctly aligned to the optical and the integral impulse tube axis.

2. That the level of image illumination detected by the central photodetector 32 is a predetermined level less than the mean of that detected by the outer detectors 34A, 34B. This condition is a gauge of the quality of focus of the image (as well as the alignment to some extent) and determines that the cornea is the correct distance away from both the objective lens and the integral impulse tube. Under these circumstances the pressure of the fluid pulse incident on the cornea will be calibrated satisfactorily relative to the internal measuring system in the tonometer and the electronic system then provides a signal to indicate that this alignment is satisfactory.

3. That the conditions described above have been maintained for a predetermined time period. This ensures that the stability of the tonometer is satisfactory for a reliable measurement to be taken and, if so, the electronic system then initiates the fluid impulse and records the applanation event.

In practice a rise time of between 5 and 20 msec has been found to be satisfactory for the pressure pulse, with applanation of a normal pressure eye typically occurring in a range of 1 to 5 msec. By choosing an alignment stability test time in the range 10 to 100 msec the instrument will then normally provide reliable readings. Satisfactory stability of this order can be achieved with hand-held operation by the operator slowly moving the instrument through and around the perceived correct visual alignment condition until it automatically fires. The instrument is thus convenient and fast to use. Typical times to achieve alignment are only a few seconds.

A lens 61 is placed at a distance equal to its focal length from the plane of the photodiodes. Its function is to sharpen up the change in contrast with distance from the eye and to ensure that there is a major change in the contrast at the applanation event over the full working range of the instrument. This is achieved by providing an aperture in the central region of the lens through which light from a correctly aligned image will pass. However with mis-alignment or during the event when the image illumination is incident on the lens 61, the latter acts to focus the light down onto the central photodiode, decreasing the contrast.

Figure 5:
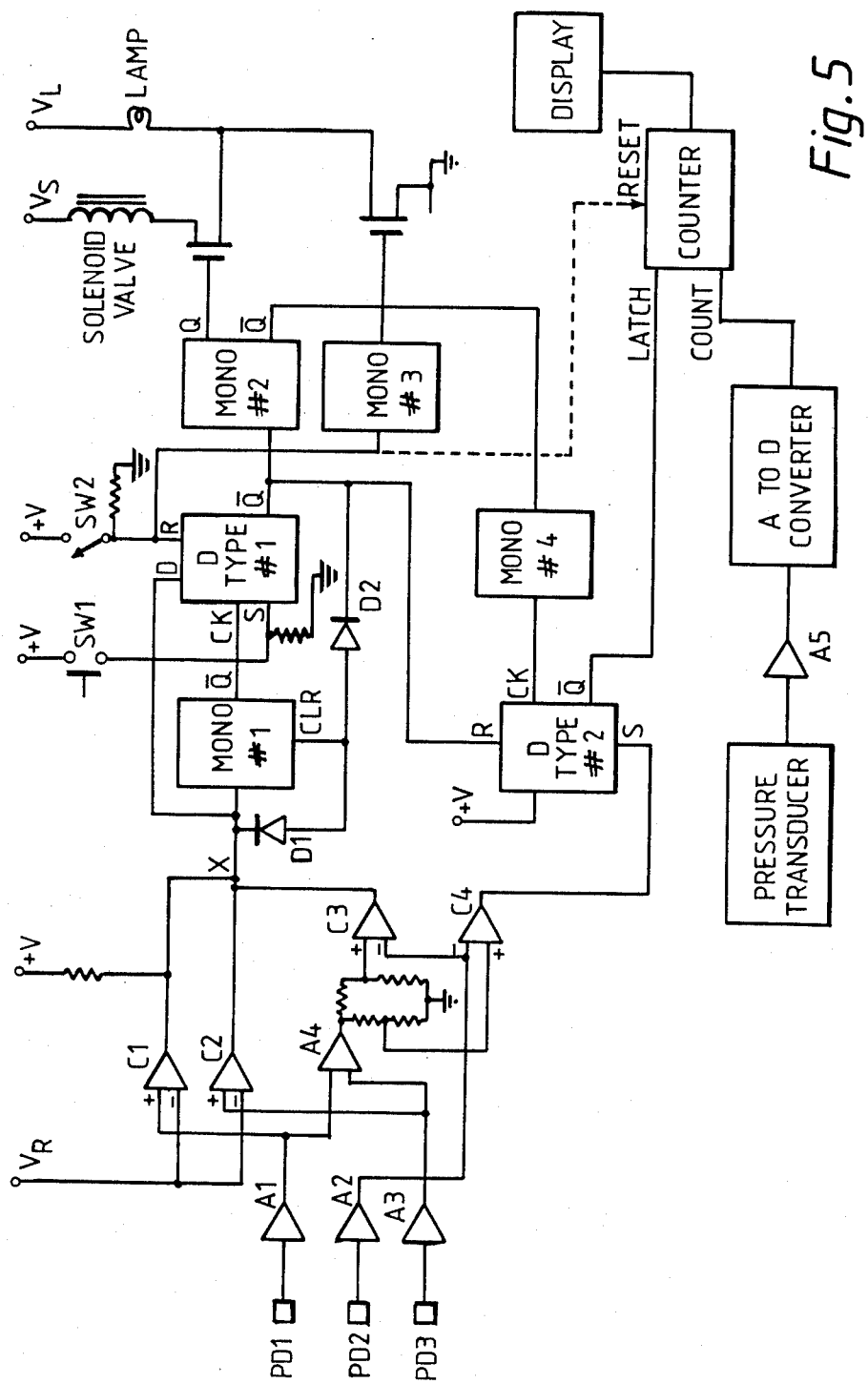
FIG. 5 is a schematic circuit diagram.

The electronic circuitry of the tonometer is shown in FIG. 5, and the essential components thereof will be apparent from the ensuing description.

Photodiodes PD1 and PD3 are arranged to pick up bright areas of the image, whilst PD2 is arranged to pick up a dark area.

Comparators C1 and C2 compare the signals from PD1 via amplifier A1 and PD3 via amplifier A3 with a reference level.

Comparator C4 determines when the ratio of the sum of the amplified signals from PD1 and PD3 to the amplified signal from PD2 is less than a fixed amount. This condition is used to determine when the applanation event occurs. Thus the output of C4 is used to provide an event signal to latch the counter via D type flip-flop No. 2.

The outputs of comparators C1, C2 and C3 are combined together so that point X is only high if all three positive inputs to the comparators are greater than the reference levels on the negative inputs. This condition is used to determine that the instrument is correctly aligned and at a correct distance from the eye.

The first monostable circuit and the first D type flip-flop are used to test that the alignment and distance condition still exists after a fixed period of time (of the order of tens of milliseconds). If this is so, the rising edge at the end of the monostable pulse clocks the alignment signal through to $\overline{Q}$ of D type flip-flop No. 1 as a high to low transition. This transition starts monostable No. 2, which turns on the solenoid to provide the pressure pulse and it also enables D type flip-flop No. 2.

Diode D2 is used to ensure that the first monostable stays in cleared state whilst the applanation event occurs. It thus inhibits any additional transition on the input to the monostable from changing the output. Diode D1 is used to clear the monostable if the signal drops out before the end of the fixed time period determined by the pulse from the monostable (Mono 1). If this signal drops out, Mono 1 is cleared, its $\overline{Q}$ output goes high, clocking the D-type flip-flop 1. Since the signal has dropped out the data on the D input of the D-type flip-flop 1 is low and thus its $\overline{Q}$ output remains low when clocked by the mono 1.

The pressure transducer monitors the rise of the applied air pulse with time. The analogue output is then converted to digital form by the A/D converter and the resultant pulses are used to increment the counter.

As soon as the event signal comes through from C4, this sets the second D type flip-flop causing the $\overline{Q}$ output to switch and provides a signal to latch the counter. The display then indicates the pressure at which the applanation event occurred.

On removing the unit 100 from the recess 118 and turning on switch 103, power is supplied to the circuits contained within the unit 100 (and any within the case). A further switch 105 is also operated automatically on removal, to enable the pump (not shown) located within the case 102.

On power-up, closing and holding closed switch SW2 (see FIG. 5), puts D-type 1 into reset condition. In this condition Mono 1 is inhibited from firing the solenoid.

If an operating test is required, SW2 is released (to open the switch) and SW1 is momentarily depressed, to simulate a high at point X. This corresponds to the condition which obtains just prior to the firing of the solenoid during an actual test on a patient, and results in Mono 2 firing the solenoid, even though no patient is involved.

Since during this simulation no output signal will normally have been generated by C4, D-type 2 will not have been set. After the firing pulse from the Mono 2, Mono 4 clocks D-type 2 after the presure pulse has finished thereby clocking a low to the latch input of the counter. The count value displayed as a result of the test will be the peak pressure measured by the pressure transducer during the test.

The counter may be reset as shown by deriving a reset signal from the reset input to the D-type 1 flip-flop.

The circuits shown in FIG. 5 and described above require the operator to operate switch SW2 and then locate the unit 100 approximately in the correct position for a measurement to be made on a patient's eye, before releasing the switch SW2. On release the reset signal is removed from D-type 1 thus enabling the latter to respond to any data signal from the point X, which will arise when the unit is correctly aligned with the eye of the patient, thus automatically triggering the solenoid.

If a different mode of operation is required in which the operator is to position the unit 100 approximately in the correct position before operating any switches, then the switch SW2 must be replaced by a normally closed switch which on being depressed, removes the reset signal from D-type 1 flip-flop and enables it to respond to a data signal from junction X as previously described.

The invention thus provides a system which is non-contact and is less critical on the precise shape of the pressure/time profile of the fluid pulse which is applied to the patient's cornea. In addition, the invention proposes an optical and electronic system which automatically fires the pressure pulse when the correct condition of distance, alignment and stability of the instrument is achieved in relation to the patient's cornea. A visual system is provided to enable the operator to obtain alignment to the approximate region in which the automatic system will function.

It should be noted that the tonometer uses image contrast to gauge the shape of the cornea. This is a much better technique than prior art systems, which rely on the total amount of collected light.

The described tonometer also has the following features:

1. The instrument measures the change in shape of the corneal surface caused by the application of a fluid pulse, using a system which inter alia incorporates a series of lenses combined with the convex reflecting surface of the cornea to form an image of a test object onto an array of photodetectors. The detectors measure the image contrast to determine when the image is in focus and thus when the instrument is correctly aligned with and spaced from a patient's eye. When the localised portion of the cornea which is used for imaging becomes distorted by an applied fluid pulse the contrast in the image reduces and the signal from the photodetectors is used to measure this reduction and relate it to the intraocular pressure as measured with conventional contacting instruments at applanation. It is this occurance which is referred to as the applanation event.

2. Use of a system to gauge the pressure pulse incident upon the cornea by monitoring the pressure at a point in the fluid delivery system or simulating the applanation measuring environment and monitoring the air pressure thereat. With this scheme it is not necessary to provide a tightly defined pressure pulse/time profile from the fluid delivery system.

3. Detection of variations in alignment of the instrument from changes in the image of the test object formed by the lenses and the corneal surface onto the photodetectors. Use is made of both the contrast in the image and the total signal in the bright areas of the image. A visual image of the test object is also provided so that the user can obtain approximate alignment.

4. Use of a series of pressure reservoirs and connecting tubes to control the pressure/time profile of the fluid pulse, which is applied to the corneal surface.

5. Detection of alignment stability using an electronic circuit to test that the conditions described in 3 are maintained for a fixed period of time.

6. Use of an automatic electronic monitoring system which actuates the pressure pulse automatically when the correct alignment and distance of the instrument is achieved relative to the cornea of the patient.

Figure 6:
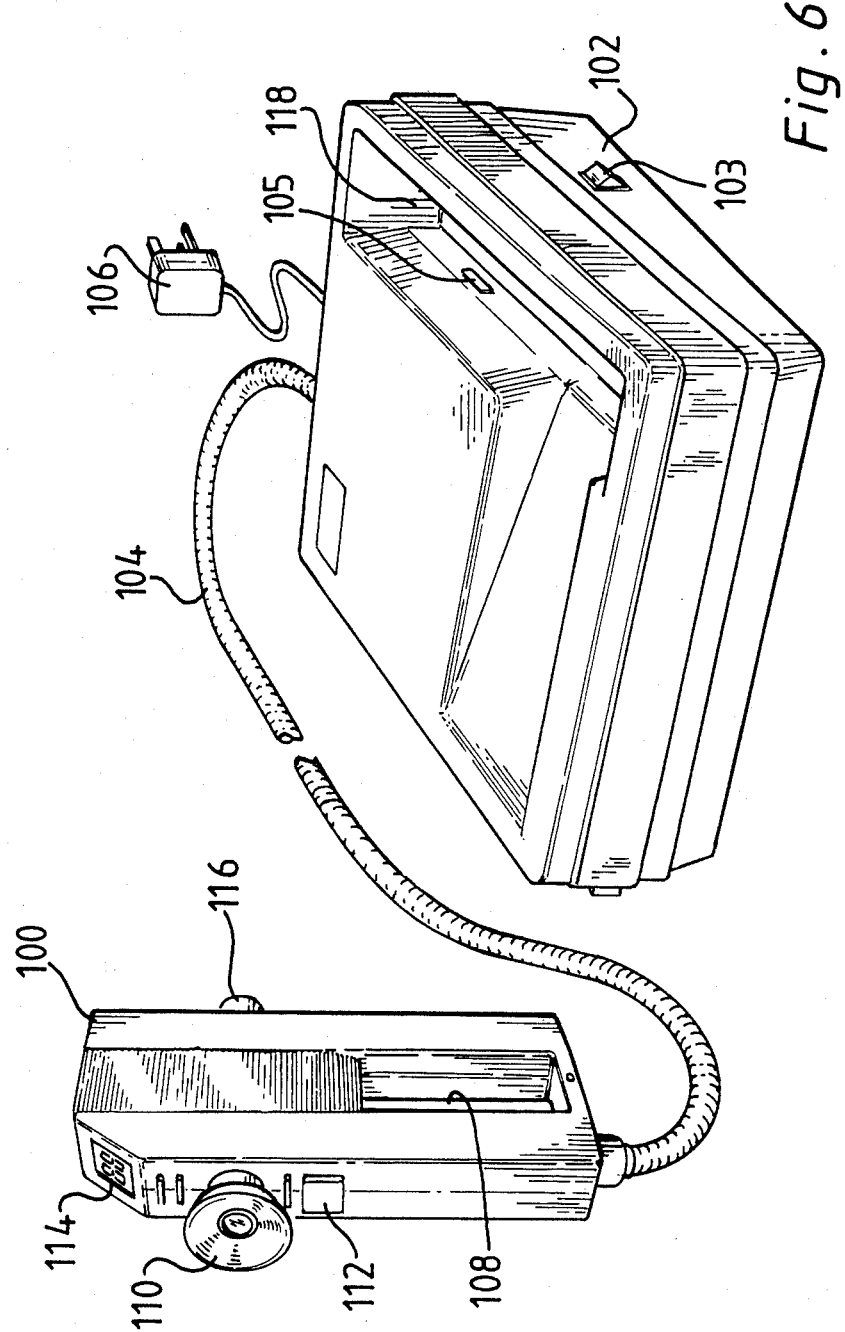
FIG. 6 is a view of a portable tonometer embodying the present invention.

FIG. 6 shows a portable tonometer embodying the present invention. The tonometer comprises a hand-held unit 100 and a case 102 connected by a flexible line 104. The case 102 serves as a carrying case for the hand-held unit 100, and also contains some of the components of the tonometer. For example, the case 102 could also contain electric batteries to power the tonometer. Alternatively, or in addition, the case 102 may be provided with a plug 106 for connection to a mains electricity supply and a transformer or other power supply regulating means may be housed in the case 102. In this case, the flexible line 104 carries the electricity supply for the components housed in the hand-held unit 100.

It may also be convenient to house an air compressor (or compressed fluid reservoir if a fluid other than air is used) in the case 102, and provide a fluid conduit in the connection line 104 as well.

In general, it is preferred if the most bulky and weighty components are housed in the case 102, so that the hand-held unit 100 is as small and light as possible. Typically, the hand-held unit 100 will incorporate the optical system and the fluid delivery tube, and at least some of the electronic control circuitry.

If a fully portable unit is required all of the control electronics may be located within the unit 100 together with a battery (typically a rechargeable cell) and a fluid reservoir, which may be either rechargeable or simply a replaceable cylinder.

The hand-held unit 100 has a hole 108 in its lower portion, which provides a handgrip for the operator. Along its rear surface, the unit 100 has an eyepiece 110 through which the operator looks into the optical system as shown in FIG. 1. Below the eyepiece 110 there is an illuminated push-button switch 112 which can be operated using the thumb of the hand used by the operator to hold the unit 100. A digital read-out display 114 is provided to show the pressure measurement count obtained from the electronic circuitry. A nozzle 116 at the front of the hand-held unit 100 houses the objective lens 10 and the fluid impulse (puff) tube 12.

In use, the case 102 is positioned on a convenient surface and is plugged into the mains electricity supply if appropriate. The user then removes the hand-held unit 100 and switches on the power switch 103 and presses the push-button 112 and checks the lamp has operated to illuminate the button. Keeping the button 112 pressed-in, the unit is positioned to approximately the correct position in front of the patient's eye, viewing the eye through the eyepiece 110 and thereby checking the image 36 (see FIG. 1). When the operator has the unit in the correct position, as determined by his view of the image 36, he releases the trigger button 112. This arms the fluid pulse providing system, but does not fire it. As the operator continues to move the hand-held unit 100 in a slow and steady manner, the electronics determines when the criteria for correct alignment, spacing and stability are met and then fires the fluid pulse. Following the applanation event, the display 114 provides a figure corresponding to the intra-ocular pressure of the patient's eye.

When the tonometer of FIG. 6 is not being used, the hand-held unit 100 can conveniently be stored in a recess 118 provided in the case 102.

In another arrangement the case 102 may be modified to allow it to be surface mounted in the manner shown or, if preferred, mounted on a vertical surface such as a wall.

Figure 7:
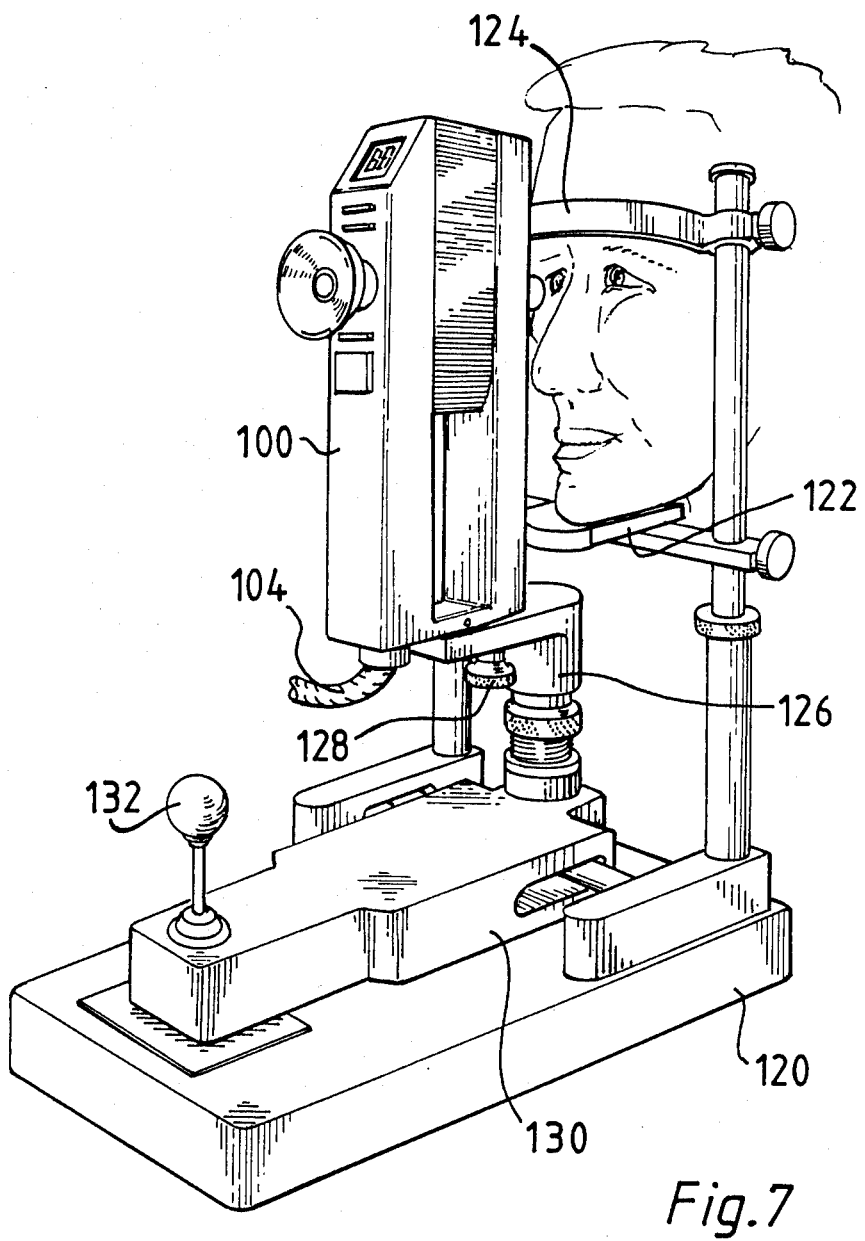
FIG. 7 is a view of an arrangement for using the hardheld unit of FIG. 6 as part of a bench mounted unit.

FIG. 7 shows a bench mounted tonometer system, which incorporates the hand-held unit of FIG. 6. A bench mounted jig 120 provides means for locating the patient's head and means for moving the hand held unit 100 in a controlled manner. The unit 100 may be mounted permanently on the jig. Alternatively, it may be found convenient to use the same unit 100 both as part of a bench-mounted system as shown in FIG. 7 and as part of a portable system as shown in FIG. 6 at different times.

In the bench-mounted system of FIG. 7, the parts of the tonometer which are not provided in the unit 100 may be provided in a case 102 as shown in FIG. 6. Alternatively, these components may be provided in a permanent installation located near the jig 120.

The jig 120 has an adjustable chin rest 122 and an adjustable forehead rest 124 for a patient, mounted at the front end of the jig 120. By use of the chin rest 122 and the forehead rest 124 a patient can hold his or her head steady while the intra-ocular pressure is being measured. A bracket 126 supports the unit 100 immediately behind the chin rest 122 and forehead rest 124. The unit 100 is attached to the bracket 126 by a screw 128.

The bracket 126 is supported on a moveable block 130, and at the rear end of the block 130 a lever 132 allows the operator to move the block 130 forwards and backwards and side-to-side in a gradual and controlled manner. As the block 130 moves, it carries the unit 100 with it by means of the bracket 126.

The bench mounted system FIG. 7 is used in the same manner as the portable system of FIG. 6, except that the operator does not position the unit 100 by moving his hand but instead moves the unit by operating the lever 132.

In FIG. 7, the bench mounted tonometer has been shown using the hand-held unit of the portable tonometer of FIG. 6. This arrangement may be advantageous as it permits a complete tonometer system which is very flexible, and which may be configured both as a portable and as a bench-mounted system with some parts being used in both cases. However, it should be appreciated that the apparatus mounted on the jig 120 need not be useable in addition as part of a portable apparatus.

I claim:

1. A tonometer comprising:
   an optical system for forming, in conjunction with the reflecting surface of the cornea of the eye, an image of a target;
   means for projecting a controlled pressure fluid pulse on to the eye to distort the corneal surface and thereby produce change in the target image;
   detecting means comprising a plurality of detectors located in the image plane respectively to be responsive to points of the target image of differing light intensities;
   means for comparing the outputs of the respective detectors to determine image contrast based on the light intensity detected by respective of said plurality of detectors and for determining the change in image contrast which occurs when the eye is distorted by the fluid pulse; and
   means for outputting a value indicative of the pressure of the applied fluid pulse at the time when the change in the image occurs.

2. A tonometer according to claim 1 further comprising pressure sensing means and means to apply pressure to the pressure sensing means whereby the pressure applied to the pressure sensing means is related in a known manner to the pressure of the applied fluid pulse and the said output value is obtained from the said pressure sensing means.

3. A tonometer according to claim 1 further comprising control means for the said projecting means which control means is responsive to the said image of the target to detect correct relative positioning between the tonometer and the said cornea to actuate the said means for projecting when the said correct relative positioning is detected.

4. A tonometer according to claim 1, in which said means for comparing said output is responsive to the ratio of said differing light intensities.

5. A tonometer according to claim 1, in which said means for comparing said output is measured as the ratio of the difference between the mean value of outputs from two outer photo detectors and the output from an inner photo detector, divided by the sum of said mean value and said inner photo detector output.

6. A tonometer according to claim 1, in which said value indicative of the pressure of the applied fluid pulse is derived from a measurement of the fluid pressure at a point where the fluid pressure bears a known relationship to the pressure of the fluid pulse.

7. A tonometer according to claim 6, further comprising a source of pressurized fluid, a fluid delivery line from said source to an outlet through which the fluid pulse is applied to the cornea, pressurized fluid flowing from the source along the delivery line to the outlet when the fluid pulse is applied, and a branch in the fluid delivery line leading to said measurement point of known relationship, said branch comprising fluid impedance means and fluid reservoir means which cause the fluid pressure at said point to match the pressure of the fluid pulse on the cornea when the outlet is in correct positioning relative to the cornea.

8. A tonometer according to claim 7, in which said outlet has a predetermined spacing from the cornea for said correct positioning to be occupied.

9. A tonometer according to claim 6, further comprising a source of pressurized fluid, a fluid delivery line from said source to an outlet through which the fluid delivery line from said source to an outlet through which the fluid pulse is applied to the cornea, pressurized fluid from the source along the delivery line to the outlet when the fluid pulse is applied, and a branch in the fluid delivery line leading to a fluid space containing said measurement point of known relationship, said branch providing a fluid impedance matching the fluid impedance in the supply line from the point where the branch leaves the supply line to said outlet, and the distance across the fluid space from the end of said branch to said pressure measurement point matching the distance from the outlet to the cornea when the outlet is in correct positioning relative to the cornea.

10. A tonometer according to claim 9, in which said outlet has a predetermined alignment with the cornea for said correct positioning to be occupied, and said pulse is applied to the cornea when said correct positioning has been occupied for a predetermined period.

11. A tonometer comprising:
an optical system for forming, in conjunction with the reflecting surface of the cornea of the eye, an image of a target;
means for detecting the initial condition of the target image to determine when the optical system has a selected predetermined location relative to the eye;
means associated with the optical system for projecting a controlled pressure fluid pulse on to the eye to distort the corneal surface and thereby produce change in the target image;
means responsive to the target initial condition detecting means for causing operation of the fluid pulse projecting means when said selected predetermined location is attained;
detecting means comprising a plurality of detectors located in the image plane respectively to be responsive to points of the target image of differing light intensities;
means for comparing the outputs of the respective detectors to determine image contrast based on the light intensity detected by respective of said plurality of detectors and for determining the change in image contrast which occurs when the eye is distorted by the fluid pulse; and
means for determining the pressure of the applied fluid pulse at the time when a given change in image contrast occurs.

12. A tonometer according to claim 11 further comprising means which detects when correct positioning relative to the eye has been effected, said means controlling the fluid delivery system so that the fluid pulse is automatically projected when correct positioning has been achieved.

13. A tonometr according to claim 12 wherein the means which detects correct positioning comprises means for detecting axial alignment with respect to the eye by measuring the output of each of a plurality of off-axis detectors, measuring the level of an on-axis detector and comparing it with the outputs of the off-axis detectors.

14. A tonometer according to claim 13 wherein said axial alignment detecting means also includes means for testing that an alignment and distance condition still exists after a predetermined period of time following an initial detection of axial alignment.

15. A tonometer comprising:
a portable casing having a handgrip;
an optical system in the casing for forming, in conjunction with the reflecting surface of the cornea of the eye, an image of a target;
means in the casing for projecting a controlled-pressure fluid pulse on to the eye to distort the corneal surface and thereby produce change in the target image;
a fluid pressure delivery system which delivers fluid to said fluid pulse projecting means;
a trigger associated with the handgrip for arming the fluid pressure delivery system;
means for detecting the target image;
means for automatically effecting the delivery of a controlled fluid pulse from the armed delivery system to the fluid projecting means when the detecting means detects a given target condition;
detecting means comprising a plurality of detectors located in the image plane respectively to be responsive to points of the target image of differing light intensities;
means for comparing the outputs of the respective detectors to determine image contrast based on the light intensity detected by respective of said plurality of detectors and for determining the change in image contrast which occurs when the eye is distorted by the fluid pulse; and means for determining the pressure of the applied pulse at the time when said given change in the target image occurs.

16. A tonometer according to claim 15 further comprising means which detects when correct positioning relative to the eye has been effected, said means controlling the fluid delivery system so that fluid pulse is automatically projected when correct positioning has been achieved.

17. A tonometer according to claim 16 wherein the means which detects correct positioning comprises means for detecting axial alignment with respect to the eye by measuring the output of each of a plurality of off-axis detectors, measuring the output of an on-axis detector and comparing it with the ouputs of the off-axis detectors.

18. A tonometer according to claim 17 wherein said axial alignment detecting means also includes means for testing that an alignment and distance condition still exists after a predetermined period of time following an initial detection of axial alignment.

19. A tonometer comprising:

an optical system for forming, in conjunction with the reflecting surface of the cornea of the eye, an image of a target;

means for projecting a controlled-pressure fluid pulse on to the eye to distort the corneal surface and thereby produce change in the target image;

detecting means comprising a plurality of detectors located in the image plane respectively to be responsive to points of the target image of differing light intensities;

means for comparing the outputs of the respective detectors to determine image contrast base on the light intensity detected by respective of said plurality of detectors and for determining the change in image contrast which occurs when the eye is distorted by the fluid pulse;

a pressure delivery system which delivers the fluid to said fluid pulse projecting means;

a pressure transducer for monitoring the pressure within the pressure delivery system; and means for matching the monitored pressure to the pressure applied to the corneal surface, whereby the pressure transducer provides a signal output indicative of the pressure applied to the eye at the time when a given target image change occurs.

20. A tonometer according to claim 19 wherein the matching means comprises a branch in the pressure delivery system where conditions are controlled to match a predetermined time/pressure profile to which the eye is subjected, and wherein the pressure transducer is located in said branch.

* * * * *